United States Patent [19]

Villaume et al.

[11] 4,040,743
[45] Aug. 9, 1977

[54] METHOD AND APPARATUS FOR MEASURING THE BRIGHTNESS OF PULP SLURRY

[75] Inventors: Henry F. Villaume, Intervale, N.H.; D. Stephen Collins, Bridgton, Maine; Patrick J. Peoples, Intervale, N.H.

[73] Assignee: Howell Laboratories, Incorporated, Bridgton, Maine

[21] Appl. No.: 615,584

[22] Filed: Sept. 22, 1975

[51] Int. Cl.$^2$ ............... G01N 21/00; G01N 21/26
[52] U.S. Cl. ............... 356/73; 162/263; 250/227; 250/565; 356/104; 356/206; 356/208
[58] Field of Search ............... 162/263; 356/73, 104, 356/181, 205, 206, 208; 250/575, 565

[56] References Cited
U.S. PATENT DOCUMENTS

| 3,498,719 | 3/1970 | Wing et al. | 356/208 |
| 3,586,862 | 6/1971 | Topol | 356/208 |
| 3,827,808 | 8/1974 | Cho | 356/199 |

Primary Examiner—Vincent P. McGraw
Attorney, Agent, or Firm—Richard L. Stevens

[57] ABSTRACT

A meter for measuring the brightness and/or consistency of pulp slurry. An optical probe introduces light energy into the slurry, which energy is transmitted and back-scattered, and reflected orthogonally. Three signals are provided which correspond to the back-scattered, reflected, and transmitted energy. Each of the signals is ratioed against a reference signal which corresponds to the intensity of the energy introduced into the slurry to provide three outputs proportional to the difference between the reference signal and the received signals. The output corresponding to the back-scattered energy is multiplied by the log of the output corresponding to the transmitted energy to produce a measurement of brightness independent of consistency. The output corresponding to the back-scattered energy is divided by the log of the output corresponding to the reflected energy to produce a measurement of consistency which is independent of the pulp brightness.

31 Claims, 9 Drawing Figures

METHOD AND APPARATUS FOR MEASURING THE BRIGHTNESS OF PULP SLURRY

BACKGROUND OF THE INVENTION

In the commercial production of paper, several measurements are required to insure consistent quality of the final product. One such measurement is the brightness of the pulp. (See TAPPI Standard T217 OS-48.) This measurement is directed to the "whiteness" of the pulp.

Instruments generally available and used for such brightness measurements deal primarily with reflective measurements and are normally off-line instruments. In these off-line instruments, a sample is periodically taken from the pulp washer, dried, and its brightness determined by a reflectance meter. This determination usually takes 20-30 minutes.

One on-line system uses two sensors disposed in the pulp such as on the stock line and measures influx and efflux of a given bleaching stage. The two measurements are compared and the results used to control bleaching chemicals in order to optimize the brightness of the pulp. It appears each sensor measures the back scatter of light in the slurry in the stock line.

A second on-line sensor compares the response of slurry to two wavelengths. Although the exact function of this instrument is not known, it is possible that the two wavelengths are chosen so that one responds to the color of the slurry and one responds to the color of the pulp liquor. This method would be dependent upon the consistency of the pulp. Alternatively, it could be that the response of the liquid is constant for the two wavelengths chosen over the range of process conditions used. In this case, the brightness measurement would be a function of the ratio of the two signals. For a discussion of types and wavelengths generated by reflectance, see Practical Aspects of Diffuse Reflectance Spectroscopy, American Laboratory, March, 1975, pages 55-64.

The meters used for brightness measurements of fibers in a slurry are generally simple reflective measurements of light transmitted into or through the pulp slurry based primarily on back-scatter reflectance.

In measuring the properties of a pulp slurry, the brightness of the pulp fiber is the property to be measured. When simple reflective measurements are used as described above, i.e., back-scatter, such a measurement is dependent upon at least two variables; namely, the fiber color itself which is the property to be measured and the consistency of the pulp slurry. The higher the percent consistency, the greater the back-scatter. A third variable may or may not be important: the pulp liquor color. Thus, present day reflective measurements of on-line instrumentation or of measurements off-line when the measurement is taken from the slurry are affected by the pulp consistency resulting in erroneous readings if the pulp consistency is not specifically analyzed and accounted for.

SUMMARY OF THE INVENTION

The present invention is directed to a method and apparatus for measuring a property of a pulp slurry, particularly pulp brightness, which eliminates in the measurement one of two dependent variables, namely, pulp consistency. In an alternative embodiment of the invention, pulp consistency can be measured, eliminating the then unwanted dependent variable of fiber color.

More particularly, the present invention includes a method and apparatus for measuring either pulp brightness or pulp consistency by transmitting into and illuminating a pulp slurry with radiant energy and measuring at a plurality of angles the reflected energy from the pulp slurry. The reflected energy is converted to signals and the signals processed one as a function of the other such that the undesired dependent variable is eliminated and a true measurement provided.

The invention broadly comprises an optical probe having an optical system which transmits radiant energy such as light energy into the pulp slurry. The light energy illuminates the pulp slurry. The reflected light energy at any angle within the illuminated area may be measured. The reflected light energy is measured at at least two distinct angles and converted to signals. The signals are converted, one as a function of the other, which eliminates the interfering dependent variable. This concept will be more fully explained in the description of the preferred embodiment.

In one aspect of the invention, the light energy introduced into the pulp slurry is measured as transmitted energy and at two angles of reflected energy, one as back-scatter and the second at some angle orthogonal to the direction of the transmitted energy. Both reflected energies and the transmitted energy are measured and converted into signals. To determine the fiber color, i.e., brightness, a signal corresponding to the back-scattered energy is multiplied by a logarithmic function of the transmitted energy to produce a measurement corresponding to pulp brightness which eliminates the variable of pulp consistency. The back-scattered energy is converted to a signal and divided by the logarithmic of the orthogonal energy which results in a measurement corresponding to pulp consistency essentially independent of fiber color.

In another aspect of the invention, an optical sensor probe is specifically designed to insure that when used on-line and inserted into the pulp slurry the optical surfaces of the probe are continually purged by the movement of the pulp slurry.

In the preferred embodiment, the invention comprises an optical sensing probe adapted to be inserted into the pulp slurry. Optical sensors are disposed in the probe and oriented to receive and transmit light energy from three different areas of the pulp slurry. Specifically, one sensor is adapted to receive transmitted energy and is disposed opposite the point of introduction of the light source, a second sensor is adapted to receive back-scatter from reflected light energy and is adjacent the light source, and a third sensor is adapted to receive orthogonally reflected light energy from the plup slurry. Preferably, the third sensor is at a right angle to the transmitted energy. The optical measurements are converted into electrical signals, corresponding to the back-scattered energy $I_B$, the transmitted energy $I_T$, and the orthogonal energy $I_R$. These three signals are ratioed with a voltage proportional to a reference beam which preferably corresponds to the intensity of the light energy introduced into the pulp slurry $I_o$. The voltage outputs are amplified and transmitted to a signal processor wherein the outputs $V_T$ and $V_R$ are adjusted to voltages $v_t$ and $v_r$ and introduced into logarithmic function generators, the outputs of which are coupled to multiplying circuits. In the multiplying circuits, the value of $V_B$ is multiplied by log $v_t$ to provide a brightness measurement $E_B$ and divided by log $v_r$ to provide a consistency measurement $E_C$. These outputs are fed to display units providing measurements of brightness and consistency.

A further aspect of the invention is the modification of the optical sensing probe wherein it may be secured to a pipe to provide the on-line brightness and/or consistency readings without the necessity for inserting an optical sensing probe into the pulp slurry itself.

The apparatus of my invention broadly comprises means to introduce a beam of light energy into a pulp slurry to measure a property of the slurry, preferably either fiber color or consistency, which property is independent upon at least two variables. The energy is back-scattered in a first direction, reflected in a second direction, and transmitted in a third direction. The back-scattered energy, the reflected and the transmitted energy are measured and converted to electrical signals. At least one of the signals which corresponds to the reflected and/or transmitted energy is processed as a log function and combined with back-scattered energy, whereby one of the variables is eliminated in making the measurement of the pulp slurry desired, either fiber color or consistency.

The method of my invention is generally directed to introducing a beam of energy into a pulp slurry to measure a property of the slurry, which property is dependent upon at least two variables such as fiber color and pulp consistency, and wherein the energy is back-scattered in a first direction, reflected in a second direction, and transmitted in a third direction, receiving the back-scattered energy and converting said energy to a signal; receiving separately the reflected and transmitted energies and converting each of the same into a signal; means to process at least one of the signals of the reflected energy or the transmitted energy in combination with the signal corresponding to the back-scattered energy, whereby one of the variables is eliminated in making the measurement of the property of the slurry, either fiber brightness and/or pulp consistency, and displaying one of the signals.

DESCRIPTION OF THE PREFERRED EMBODIMENT

Figure 1:
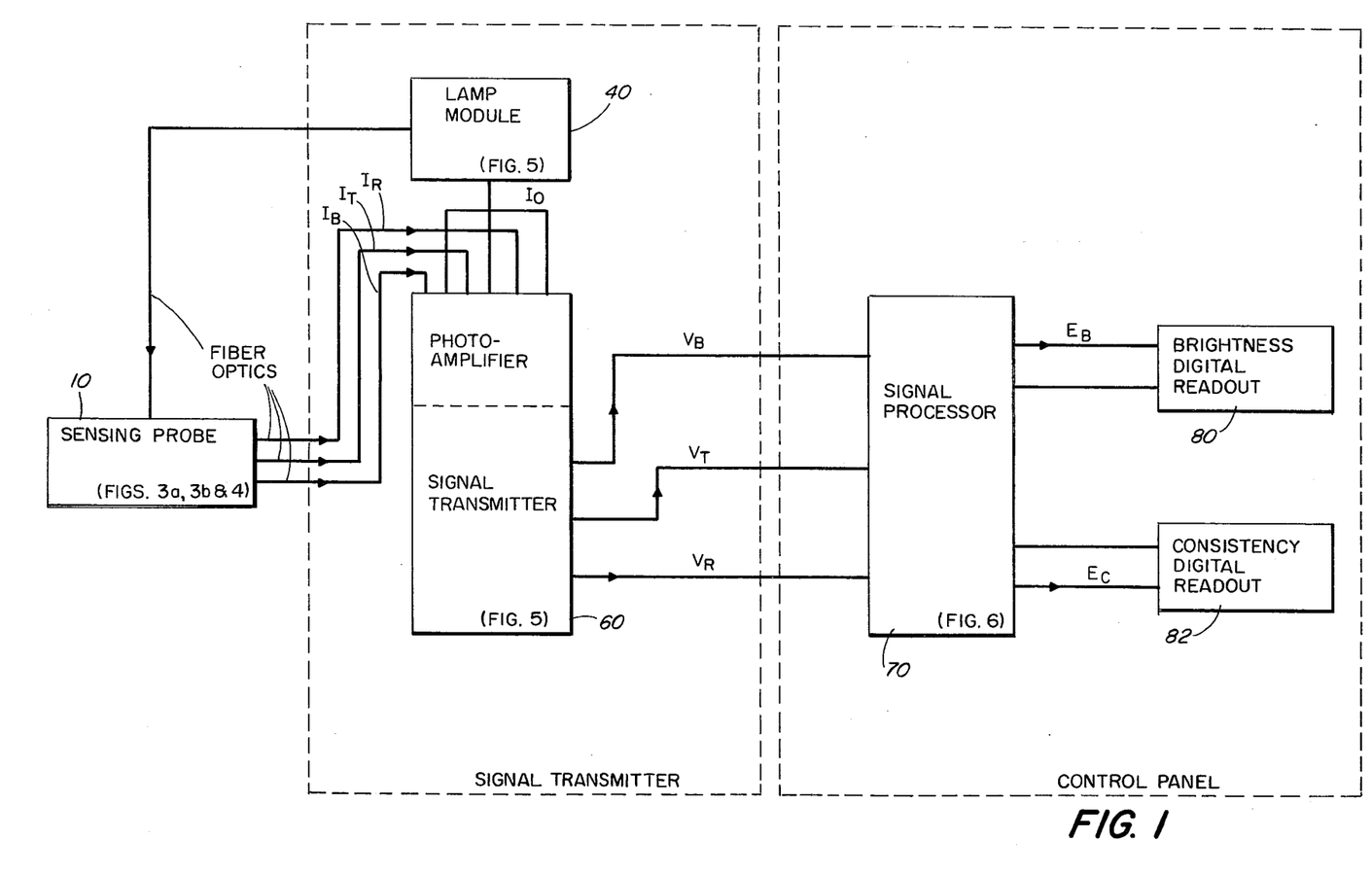
FIG. 1 is a general block diagram of the preferred embodiment of the invention.

The preferred embodiment of the invention will be illustrated in reference to a brightness measurement of pulp in a slurry which correlates to TAPPI Standard T217 OS-48 for brightness measurement. An embodiment of the invention is shown generally in FIG. 1 and includes an optical sensing probe 10 which receives light energy from a lamp module 40 and transmits light energy to a photocell module 50 and from the module 50 to a signal transmitter 60. The output from the signal transmitter 60 is received by a signal processing module 70 and which directs its output to a display unit 80.

Optical Sensing Head

Figures 2, 6:
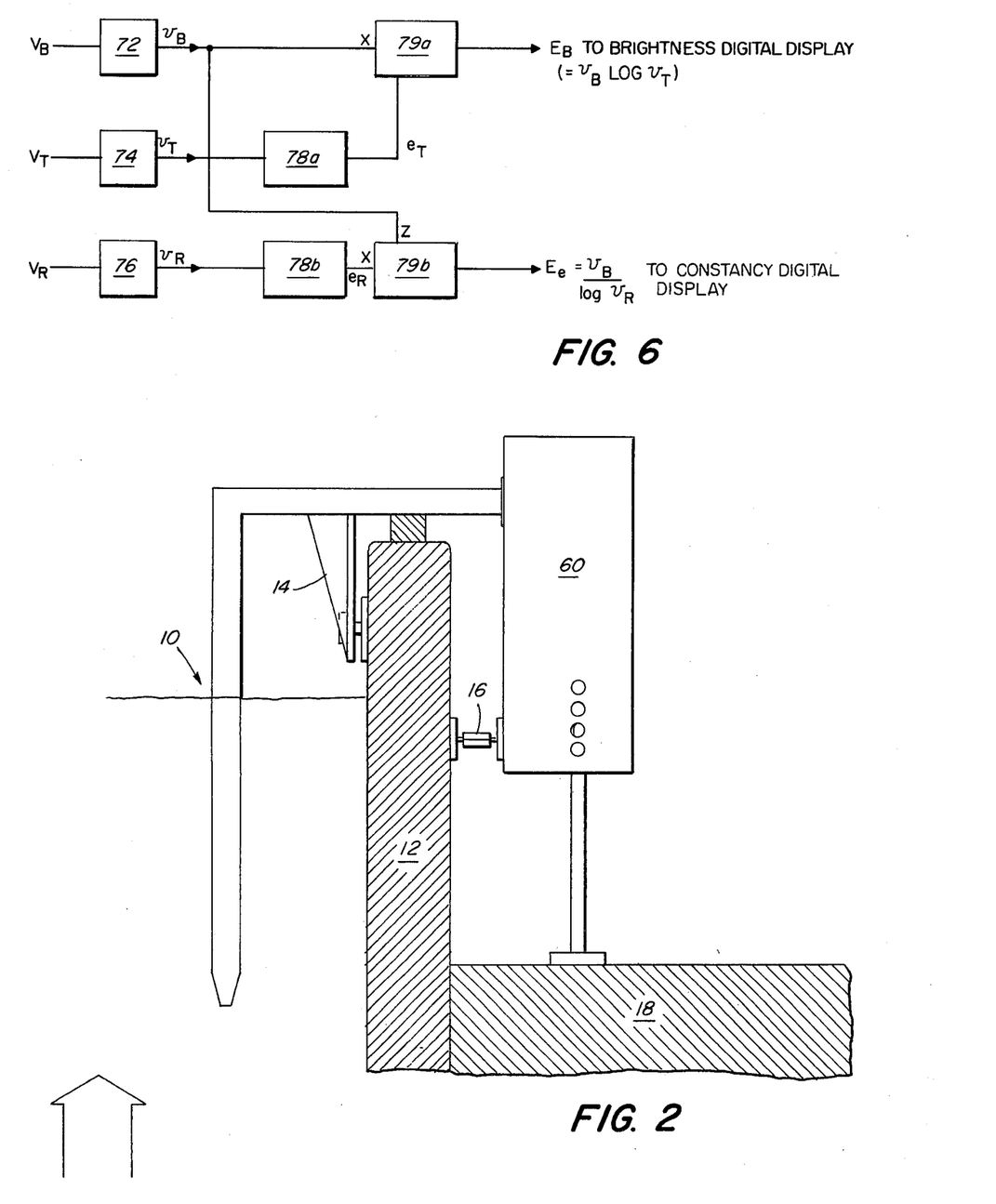
FIG. 2 is a front elevation partially sectional view of an optical sensing probe disposed in a pulp vat.
FIG. 6 is a block diagram of a signal processor.

Referring to FIG. 2, the sensing probe 10 is shown mounted to the lip of a pulp tank wall 12 by means of brackets 14 and 16. The bracket 16 is secured to the signal transmitter 60 which is in turn secured to a floor 18. The probe 10 is shown in greater detail in FIGS. 3a and b and 4 and includes four fiber optics 20, 21, 22 and 24 such as American Optical No. LGM3. A prism 26 is disposed below fiber optics 20 and 21 in optical communication therewith. The prism 26 receives the light energy from the lamp module 40 and directs it into the slurry, illuminating the slurry as indicated by the shaded area. A prism 28 is disposed below the fiber optic 24 and is in optical communication therewith. The prism 28 is adapted to receive light energy transmitted through the illuminated area and back through the fiber optic 24 to the signal transmitting unit 60. The fiber optic 22 is adapted to receive light from the illuminated area in a direction orthogonal to the transmitted light. The prism 26 and the fiber optic 21 receive back-scattered reflected light energy. Windows 30, 32, and 34 are secured in the probe 10 adjacent to the prisms 26 and 28 and the fiber optic 22.

Figure 3A:
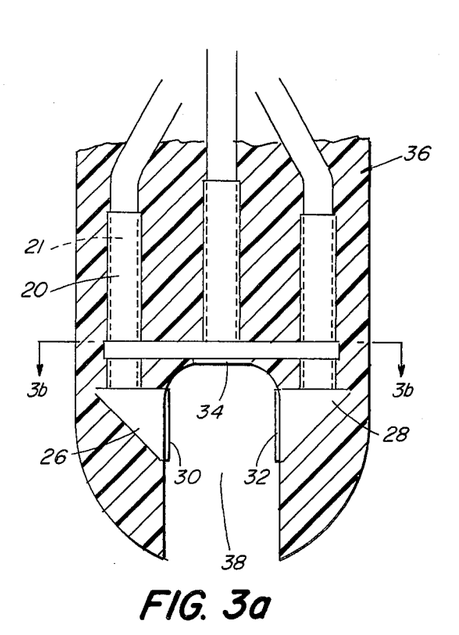
FIGS. 3a and b are front and side elevations of the optical sensing probe.
Figure 3B:
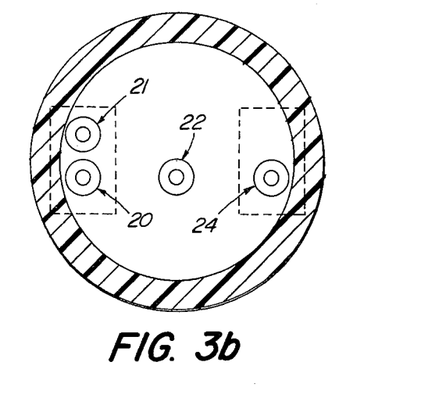
Figure 4:
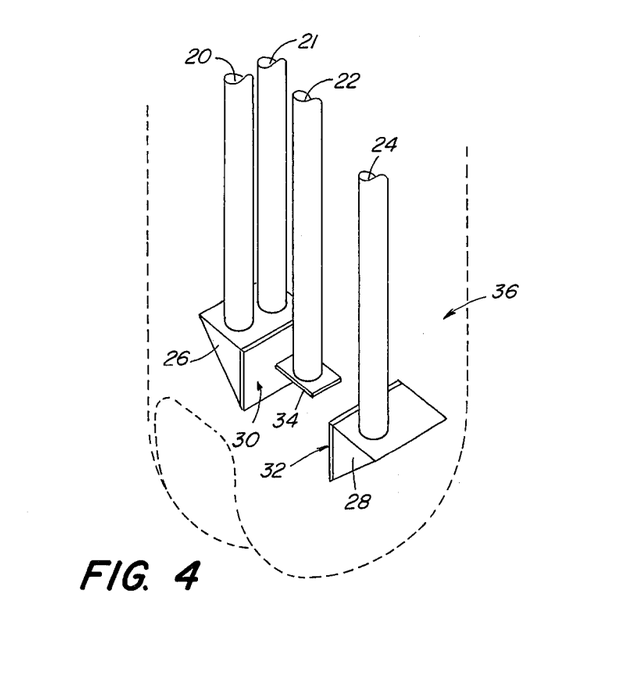
FIG. 4 is a perspective partially fragmentary view of the probe of FIG. 3.

The prisms, windows and fiber optics are all disposed in a unitary one-piece molded housing 36, such as cast epoxy, Emerson & Cummings Stycast 2651MM which is not susceptible to corrosion by chlorine gases or caustic solutions. The terminus of the probe is saddle-shaped and defines a U-shaped zone 38 and the exterior of the probe terminus is tapered such that its placement in the moving plup slurry will insure continuous purging of the windows.

Light Module Photo-Amplifier and Signal Transmitter

Figure 5:
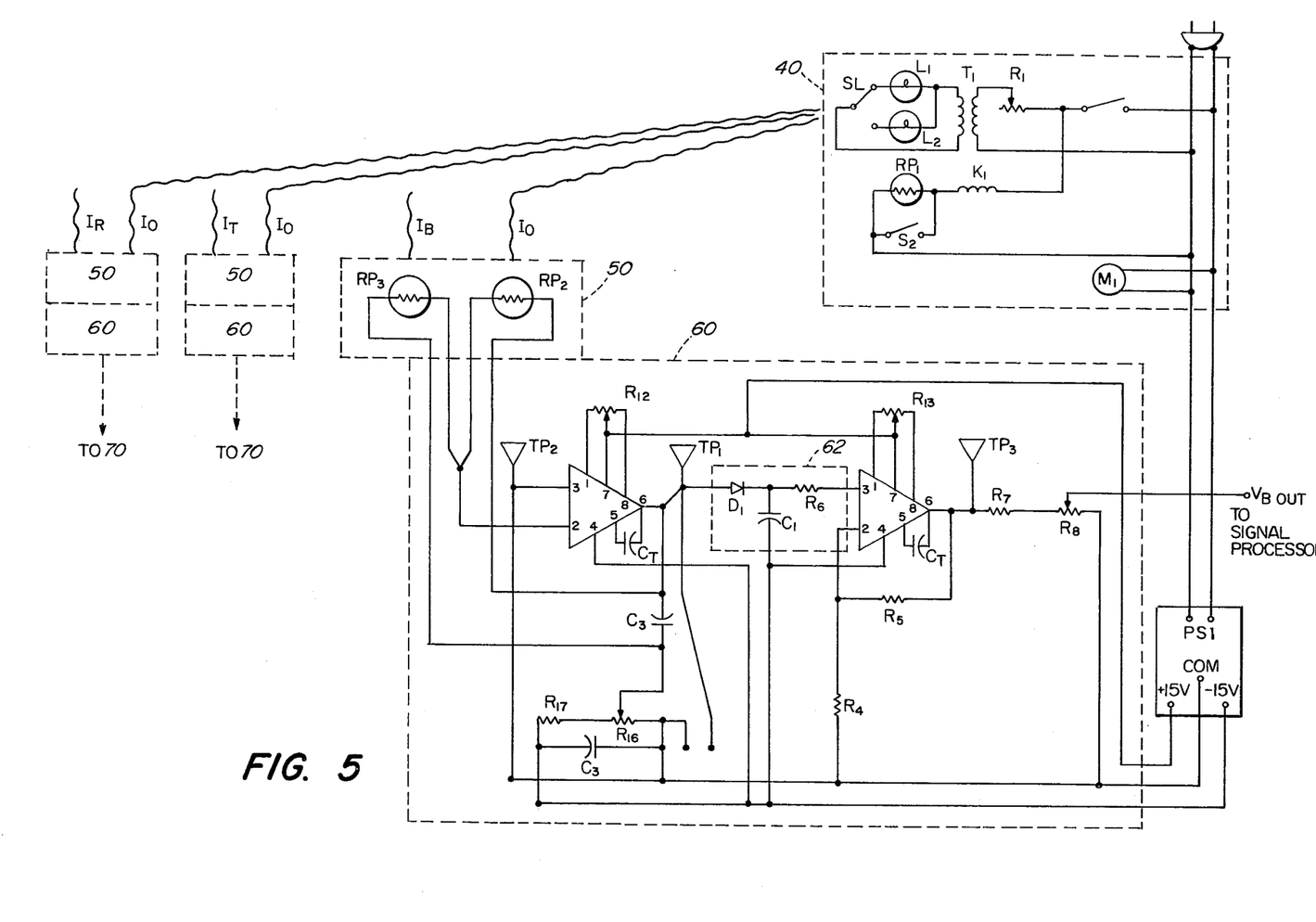
FIG. 5 is a schematic of a lamp module; and photoamplifier and signal transmitter.

Referring to FIG. 5, the lamp system 40, the photocell module 50 and the signal transmitting module 60 are shown. Only one lamp system is required in this embodiment. Three photocell modules 50 and signal transmitters 60 are required. However, in that they are identical, only one photocell module 50 and signal transmitter 60 will be described in detail. The photocell module 50 essentially provides a balanced input circuit. Photoresistors $RP_2$ and $RP_3$ receive the optical input $I_o$ and $I_B$. The $I_o$ source is received directly from the lamp module as shown, it being understood that similar circuits exist for $I_o$, $I_R$ and $I_o$, $I_T$. These photoresistors $RP_2$ and $RP_3$ convert changes in light energy to changes in electrical resistance. Power is supplied to the photocell module by the power supply PS-1 such as a Philbrick 2204 to provide a ±15 volt range.

The signal transmitter 60 includes a ratiometric amplifier A-1 and resistor R-12 and capacitor CT, which control the offset voltage and frequency compensation of the amplifier A-1. A sample-and-hold circuit 62 comprises diodes D-1 and capacitor C-1 and resistor R-6 which circuit is responsive to output from the amplifier A-1. The output from the sample-and-hold circuit is received by a second amplifier A-2 which transmits its output to the signal processor 70.

Signal Processor

The signal processor 70 includes three scalers 72, 74 and 76 which accept signals $V_B$, $V_T$, and $V_R$ and scales them to the $v_B$, $v_T$, and $v_R$ respectively. The scalers are triple buffer amplifiers, Fairchild A7351. The output of the scalers 74 and 76 for $v_T$ and $v_R$ is transmitted to log amplifiers 78a and 78b such as Analog Devices No. AD756's and produce outputs $e_T e_R$ (Log $v_T$, Log $v_R$) which enter multipliers 79a and 79b such as Fairchild AD428J's. The log function $e_T$ is multiplied by $v_B$ to generate an output $e_B(v_B \text{Log } v_T)$ brightness. This output goes to the display panel 80, such as an Analog Device 2002. A corresponding output $e_C(v_B/\text{Log } v_R)$ goes to a display panel 82.

Operation

Prior to the actual on-line use, the instrument at least once is used to analyze several known samples to provide a scale which can correlate to brightness measurement values which would result if the TAPPI procedure were used. Preferably four such readings are taken covering maximum and minimum brightness expected and two intermediate levels. The samples are also tested for brightness by the TAPPI Standard T217 OS-48. A representative chart is set forth below:

| SAMPLE | METER | TAPPI STD. |
|---|---|---|
| A | 0.60 volts | 30 |
| B | 1.20 volts | 60 |
| C | 1.60 volts | 80 |
| D | 1.75 volts | 88 |

Thus, by simple interpolation, the digital reading from the display panel 80 can be correlated to a TAPPI brightness standard. If an analog meter were used, both scales could appear and be read at the same time. Other methods of calibrating the instrument may be used such as having the minimum brightness reading correspond to 0 volts and the maximum correspond to 15 volts and the minimum and maximum displayed values corresponding to the standard minimum and maximum values.

The operation of the invention will be described in reference to a pulp slurry of up to about 5% consistency, preferably between 0.5 to 5.0%, say for example, 3% consistency, such as a Kraft pulp in a bleach vat.

As shown in FIG. 2, the probe 10 is inserted into a slurry of 3% consistency in a bleach vat. Preferably, the end of the probe 10 is inserted at least a minimum of 4 inches into the slurry. The electrical components of the instrument are powered simply by connecting to a standard line current. This connection also powers the signal processing unit 70 and display unit 80.

Referring to FIG. 5, in the lamp module 40, the transformer $T_1$ reduces the line current to 26 VAC. The variable potentiometer R-1 reduces the voltage to approximately 14 volts and serves to prolong lamp life and improve overall brightness instrument linerality. Switch S-1 activates power lamp L-1 which is a tungsten halide bulb such as a Silvania ENB-EKE. Switch S-2 is depressed momentarily, allowing current to pass through the relay coil K-1, lighting lamp L-2 and extinguishing lamp L-1. Photocell $RP_1$ is illuminated by lamp L-2 and while L-2 is radiating, the photocell $RP_1$ will hold the current through the relay coil K-1.

If the lamp L-2 fails, the current is released from relay coil K-1 and lamp L-1 is then actuated. This feature of the invention insures that if the brightness meter readings are being taken during a mill run, there is no loss because of down time in order to release a lamp. The light energy from lamp L-2 optically communicates with both photosensor $RP_3$ and fiber optic 20.

Referring to FIG. 3a, the light energy passes through the fiber optic 20, the prism 26 and the window 30 as a beam of light energy in a wavelength range of visible light with a center frequency of about 5000 angstroms. The fibers in the slurry reflect light and the fiber optics 21, 22 and 24 are orientated to accept different parts of the illuminated area. More specifically, the prism 28 accepts light energy transmitted through the slurry in the zone 38 and the fiber optic 24 transmits this light $I_T$ to a photoresistor (not shown). A second window is disposed orthogonally and specifically as in the illustrated embodiment at a right angle to the transmitted beam, whereby light reflected orthogonally $I_R$ is received and transmitted by fiber optic 22 to its associated photoresistor (not shown).

Back-scattered light energy reflected at 180° is received by prism 30 and transmitted by optic 21 back to photoresistor $RP_3$ and $I_B$ shown in FIGS. 3 and 5. Thus, three signals are received from the optical probe 10 disposed in the slurry, namely $I_B$, back-scattered reflected light energy; $I_R$, orthogonally reflected light energy; and $I_T$, light energy transmitted through the slurry. In the illustrated embodiment, the distances between the windows 30 and 34 are 1 inch and the window 22½ inch from the center line passing through the joining windows 20 and 24. The values of $I_B$, $I_R$ and $I_T$ are 2.5, 2.8 and 2.7 foot candles respectively.

The photoresistors $RP_3$ and $RP_2$ are thus illuminated by the radiation of the back-scattered light energy $I_B$ from the slurry and the source light $I_O$ respectively. Corresponding circuits for $I_T$, $I_O$ and $I_R$, $I_O$ are not described in detail, but are exactly the same as will be described for $I_B$, $I_O$ and are simply shown in block from in dotted lines in FIG. 1.

The photoresistors $RP_3$ and $RP_2$ which are the measuring and reference photocells respectively, are connected so as to form the feedback for the differential amplifier $A_1$. Thus, $RP_3$, the measuring photoresistor, is connected between the inverting input of $A_1$ and a constant voltage $V_1$; and $RP_2$, the reference photoresistor, is connected between the output and the non-inverting input of $A_1$.

Since the open loop gain of $A_1$ is large, then $$V_B = V_1 \times \text{gain} = V_1 \frac{RP_2}{RP_3}$$

where $RP_2/RP_3$ is the feedback ratio when the non-inverting input of $A_1$ is connected to power supply common and $V_B$ is the output voltage. In the linear portion of a photoresistor response, then $R_p = K/I$. Where $I$ is the illumination level of the photoresistor. Then $$RP_3 = \frac{K_3}{I_B} \quad RP_2 = \frac{K_2}{I_o}$$

where $K_3$ and $K_2$ are the proportionality constants of the measure and reference photoresistors and $I_B$ and $I_o$ are the illumination levels of the photoresistors.

The output voltage now becomes $$V_B = V_1 \frac{RP_2}{RP_3} = V_1 \frac{K_2}{I_o} \frac{I_B}{K_3}.$$

If the lamp fluctuates, then $V_o$ remains unchanged since $I_B$ and $I_o$ will change by the same percentage, since $I_B$ and $I_o$ are derived from the same lamp. However, if the fluctuation is too great then $K_2$ or $K_3$ will change in value and an apparent change in value will be observed. However, within the practical range, this does not pose a problem, and $V_B = V_1 q (I_B/I_o)$, where $q$ is a constant, describes the functioning of the circuit.

Another advantage of the circuit is that it operates best when $RP_3$ and $RP_2$ are of the same order of magnitude, so that the gain of amplifier $A_1$ is low. Since $V_1$ will be in the order of 1 volt, choosing an amplifier with low enough noise figures is simplified (greatly), since noise figures of 10 microvolts and lower are common. Thus $I_o$ is not known, but the illumination of $RP_2$ is varied until noise insensitivity is produced. The output $V_B$ of the ratiometric amplifier A-1 is directly proportional to the ratio between the back-scatter $I_B$ and input $I_o$ signals. Resistors R-12, 10 K-ohms and capacitor $C_T$ = 390 picofarads are used to control the offset voltage and low frequency conpensation of the amplifier A-1 within the range of 5mV and ±1 dB respectively.

The output $V_B$ of the operational amplifier A-1 is 5 volts and is fed into the sample-and-hold circuit 142 which comprises capacitors C-1, diode D-1 and resistor R-6, 10 M-ohms, so as to charge capacitor C-1 to higher value whenever the value applied to the anode of D-1 exceeds the voltage level applied to the cathode of the diode D-1 by the capacitor C-1. The charging time constant is 1 millisecond in this embodiment. The capacitor C-1 discharges only through the high impedence resistor R-6 plus the input impedance of the amplifier A-2 which is 20 meg-ohms. The voltage across the capacitor C-1 decays very slowly. In the present embodiment, discharge time constant is about 5 seconds. Thus, the voltage 5 volts corresponding to the actual amount of light energy back-scattered (reflected and transmitted for the corresponding circuits) is stored on capacitors C-1 and is available continuously as output to A-2. Of course, the discharging time constant may be varied as desired. The sample-and-hold circuit stabilizes and prevents flutter.

The amplifier A-2 comprises resistors R-4, one M-ohm; R-5, 1 M-ohm; R-13, 10 K-ohms; and a capacitor $C_T$ of 390 microfarads which is used to control the offset voltage and low frequency compensation within the limits of ±5 mV and ±1dB respectively. The output $V_B$ from the differential amplifier A-2 is transmitted to the signal processor 60 and is 8.0 volts, as well as the corresponding outputs $V_T$ 9.6 volts and $V_R$ 11.2 volts from identical circuits not shown.

Referring to FIG. 6, the signals $V_T$, $V_B$ and $V_R$ are received by the signal processor 70. The scalers 72, 74 and 76 accept the signals $V_T$ 9.6 volts; $V_B$ 8.0 volts; and $V_R$ 11.2 volts and scales them to $v_T$ 1.2 volts; $v_B$ 1.0 volts; and $V_R$ 1.4 volts, respectively. $v_T$ is applied to the input of the logarithmic amplifier 78b; and $v_B$ is applied to the input of the multiplier 79a.

As stated above, the illustrative embodiment is in reference to determining the on-line brightness of the fibers in a pulp slurry. Further, the amount of fibers (consistency) as opposed to the brightness of the fibers, is a function of the log of the transmission of light energy through a given volume of fibers. As the consistency increases, the amount of back-scatter increases and the amount of transmission decreases.

The output of the logarithmic function generator 78a will be $$e_t = K\log_{10}\frac{v_T - E_{os}}{E_{REF}}$$

where $E_{os}$ is the offset voltage which is 5K millivolts. Thus, when $E_{os}$ is 0.005 volts compared with $v_t$ at 1.2 volts and $E_{REF}$ and K are stable through the temperature range required, then $e_t$ is an accurate logarithm of $v_t$. The output $e_t$ of the logarithmic function generator 78a at the value of 1.61 volts is applied to the input of the multiplier 79. The output of the multiplier 79 is derived as follows:

$$E_B = \frac{v_b e_t}{10X} + \frac{x_o e_t}{10X} + \frac{v_b v_o}{10X} + Z_o + F(v_b, e_t)$$

where $X_o$ and $Y_o$ are the offset errors at the multiplier inputs used for $v_b$ and $e_t$ respectively. $X$ is a scaling factor, $Z_o$ is the output offset and $F(v_b, e_t)$ are 0.005 volts, 0.005 volts and 1% respectively and are small and stable over the temperature range required. Thus $E_B$ (output of the multiplier) = $(v_b e_t/10X) \pm 1\% + Z$ or $v_b$ at 1.0 volts times $e_t$ at 1.61 volts. Thus, $E_B$ = 1.61 volts. This is the required function of brightness. Referring to the above chart, this reading would correspond to a standard brightness of 80.

If the consistency of the above pulp changes, say to 1.5%, the values of $I_B$, $I_R$ and $I_T$ would be 2.0 feet candles. $I_o$ would remain a constant. This would result in values of $V_B$, $V_R$ and $V_T$ of 6.4 volts, 13.8 volts, and 14.4 volts, which would be scaled to $v_B$, $v_R$ and $v_T$. Multiplying in multiplier 78a, $v_B$ at 0.8 times log of $v_t$ at 2.01 volts would result in an $E_B$ of 1.61 volts or a brightness of 80. Therefore, the brightness readings are unaffected by consistency.

Figure 7:
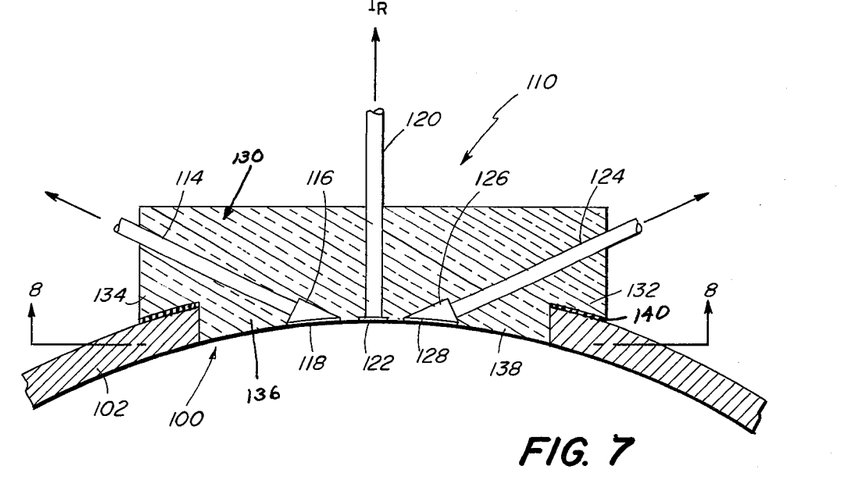
FIG. 7 is an optical probe of an alternative embodiment of the invention.

The invention has been described in reference to the optical probe being disposed in a vat. At times it may be desirable to measure the brightness (or consistency) of the pulp in another part of the total process, such as where the pulp slurry is flowing through a pipe. To accomplish this, an alternative structure for the optical probe is shown in FIG. 7. A slot-like aperture 100 is formed in a pipe wall 102. The aperture 100 is most clearly seen in FIG. 8. An optical probe 110 includes a fiber optic 112 for transmission of radiant energy $I_o$ into the slurry; a fiber optic 114 for receiving back-scattered energy $I_B$, and an associated prism 116 and a window 118; a fiber optic 120 for receiving orthogonal energy $I_R$ and an associated window 122; and a fiber optic 124 for receiving transmitted energy $I_T$ with an associated prism 126 and a window 128. The functions of the fiber optics; prisms and windows are the same as described for the preferred embodiment and will not be described in detail.

Figure 8:
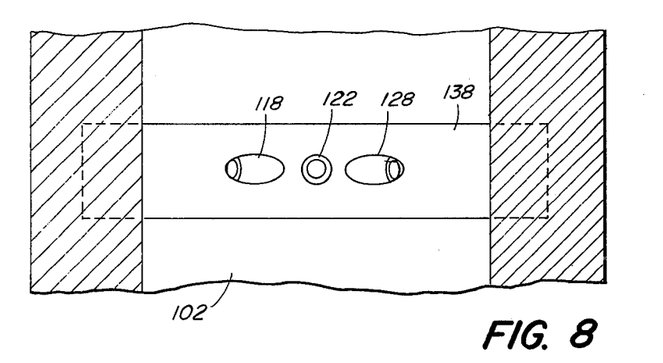
FIG. 8 is a sectional view of FIG. 7 taken along line 8—8.

A molded housing 130 secures the optics, windows and prisms in place and includes shoulders 132 and 134 and an extension 136 having an arcuate surface 138. The shoulders engage the outer surface of the pipe wall with a gasket 140 disposed therebetween. The extension 136 frictionally engages the walls of the aperture 100 and the probe 110 is secured in place by a strap 142. The arcuate surface 138 and the windows lie in the plane described by the inner surface of the pipe wall. The illuminated area is illustrated by the shaded portion and measurements may be taken as the slurry flows through the pipe.

Having described our invention, what we now claim is:

1. A brightness meter which comprises:
   a. means to introduce a beam of energy into a pulp slurry to measure a property of the slurry, which property is dependent upon at least two variables and which energy is back-scattered in a first direction, reflected in a second direction, and transmitted in a third direction;
   b. means to receive the back-scattered energy and to select the transmitted energy and to provide a selected signal;
   c. means to convert the selected signal to a log function;
   d. means to multiply the signal corresponding to the back-scattered energy with the selected signal, whereby one of the variables is eliminated in making the measurement of the desired property of the pulp slurry; and,
   e. means to display and processed measurement.

2. The meter of claim 1, wherein the means to process includes:
   means to compare the signals with a reference signal which reference signal is relative to the intensity of the energy introduced into the slurry.

3. The meter of claim 2, wherein the reference signal is a voltage proportional to the intensity of the energy introduced into the slurry.

4. The meter of claim 3 which includes:
   means to receive the reference signal and to ratio said signal to each of the signals received to provide outputs directly proportional to the difference between said reference signal and each of said received signals.

5. The meter of claim 4 wherein the means to receive and ratio the reference signal and each of the signals include photocells in combination with the first differential amplifiers.

6. The meter of claim 5 which includes means to store the signals output from the first differential amplifiers for a predetermined period of time prior to processing said signals.

7. The meter of claim 6 wherein the means to store the signals includes a sample-and-hold circuit.

8. The meter of claim 7 which includes second differential amplifiers adapted to receive the outputs of the sample-and-hold circuits.

9. The meter of claim 1 wherein the means to introduce the beam of energy includes:
   means to introduce light energy into the slurry;
   first receiving means in optical alignment with the means to introduce the light energy into the slurry, to receive light transmitted through the slurry, and to direct the light to a reference receptor, which receptor provides a signal corresponding to the transmitted light; and
   second receiving means adapted to receive light back-scattered at approximately 180° from the pulp slurry and to transmit said light to a second reference receptor, which receptor provides a signal corresponding to back-scattered light.

10. The meter of claim 1 which includes:
    means to select both the reflected and transmitted energies and to provide signals corresponding to the same;
    means to convert both selected signals to log functions;
    means to multiply the signal corresponding to the back-scattered energy by the log function of the transmitted energy and to provide a measurement corresponding to pulp brightness; and
    means to divide the signal corresponding to the back-scattered energy by the log function of the reflected energy and to provide a measurement corresponding to pulp consistency.

11. The meter of claim 10 wherein the means to introduce the beam of energy includes:
    means to introduce light energy into the slurry;
    first receiving means in optical alignment with the means to introduce the light into the slurry, to receive light transmitted through the slurry, and to direct the light to a reference receptor, which receptor provides a signal corresponding to the transmitted light;
    second receiving means disposed in a direction substantially normal to the optical path between the means to introduce the light into the slurry and the first receiving means to receive orthogonally reflected light, and to transmit the same to a reference receptor, which receptor provides a signal corresponding to orthogonally reflected light; and
    third receiving means adapted to receive light back-scattered at approximately 180° from the pulp slurry and to transmit said light to a third reference receptor, which receptor provides a signal corresponding to back-scattered light.

12. A brightness meter which comprises:
    a. means to introduce a beam of light energy into a pulp slurry to measure the pulp brightness, which property is dependent upon at least two variables, and which energy is back-scattered in a first direction, reflected in a second direction, and transmitted in a third direction;
    b. means to receive the back-scattered energy, and the transmitted energy and to provide two signals corresponding to the same;
    c. means to provide a reference signal which corresponds to the intensity of the light energy introduced into the pulp slurry;
    d. means to compare each of the two signals to the reference signal and to provide outputs directly proportional to the difference between said reference signal and each of said two signals;
    e. means to convert the output corresponding to the transmitted light energy to a log function;
    f. means to multiply the output corresponding to the back-scattered energy by the log function of the transmitted energy; and
    g. means to display said processed measurement as the brightness of the pulp slurry.

13. The meter of claim 12, wherein the means to compare the reference signal with each of the signals received from the pulp slurry includes means to ratio each signal to the reference signal.

14. A method for measuring the brightness or consistency of a pulp slurry which includes:
    a. introducing a beam of light energy into a pulp slurry to measure a property of the slurry, which property is dependent upon at least two variables and which energy is back-scattered in a first direction, reflected in a second direction, and transmitted in a third direction;
    b. providing a signal corresponding to the back-scattered energy and providing and selecting a signal corresponding to the transmitted energy.

c. converting the selected signal to a log function;
d. multiplying the signal corresponding to the back-scattered energy with the selected signal to provide a measurement corresponding to pulp brightness; and,
e. displaying said measurement.

15. The method of claim 14 which includes:
providing a reference signal corresponding to the energy introduced into the pulp slurry; and
comparing the reference signal with each of the signals to provide an output directly proportional to the difference between the reference signal and each of said signals.

16. The method of claim 15 which includes:
ratioing the reference signal to each of the signals received.

17. The method of claim 14 which includes:
selecting both the reflected and transmitted energies and providing signals corresponding to the same;
converting both selected signals to log functions;
multiplying the signal corresponding to the back-scattered energy by the log function or the transmitted energy to provide a measurement corresponding to pulp brightness; and
dividing the signal corresponding to the back-scattered energy by the log function of the reflected energy to provide a measurement corresponding to pulp consistency.

18. The method of claim 14 wherein the pulp consistency is between about 2-6%.

19. A consistency meter which comprises:
a. means to introduce a beam of energy into a pulp slurry to measure the consistency of the slurry which consistency is dependent upon at least two variables and which energy is back-scattered in a first direction, reflected in a second direction, and transmitted in a third direction;
b. means to receive the back-scattered energy and to select the reflected energy and to provide a selected signal;
c. means to convert the selected signal to a log function;
d. means to divide said log function into the signal corresponding to the back-scattered energy to provide a measurement corresponding to pulp consistency; and,
e. means to display said processed measurement.

20. The meter of claim 19 wherein the means to introduce the beam of energy includes:
means to introduce light energy into the slurry;
first receiving means disposed in a plane substantially normal to the path of the light introduced into the slurry, to receive orthogonally reflected light and to direct the light to a reference receptor, which receptor provides a signal corresponding to the reflected light; and
second receiving means adapted to receive light back-scattered at approximately 180° from the pulp slurry and to transmit said light to a second reference receptor, which receptor provides a signal corresponding to back-scattered light.

21. The meter of claim 19 wherein the means to process includes:
means to compare the signals with a reference signal, which reference signal is relative to the intensity of the energy introduced into the slurry.

22. The meter of claim 21 wherein the reference signal is a voltage proportional to the intensity of the energy introduced into the slurry.

23. The meter of claim 22 which includes:
means to receive the reference signal and to ratio said signal to each of the signals received to provide outputs directly proportional to the difference between said reference signal and each of said received signals.

24. The meter of claim 23 wherein the means to receive and ratio the reference signal and each of the signals includes photocells in combination with the first differential amplifiers.

25. The meter of claim 24 which includes means to store the signals output from the first differential amplifiers for a predetermined period of time prior to processing said signals.

26. The meter of claim 25 wherein the means to store the signals include a sample and hold circuit.

27. The meter of claim 26 which includes:
second differential amplifiers adapted to receive the outputs of the same and hold circuits.

28. A method for measuring the consistency of a pulp slurry which includes:
a. introducing a beam of light energy into a pulp slurry to measure a property of the slurry which property is dependent upon at least two variables and which energy is back-scattered in a first direction, reflected in a second direction and transmitted in a third direction;
b. providing a signal corresponding to the back-scattered energy and providing and selecting corresponding to the reflected energy;
c. converting the selected signal to a log function;
d. dividing the selected signal corresponding to the log function into the back-scattered energy to provide a measurement corresponding to pulp consistency; and,
e. displaying said measurement.

29. The method of claim 28 which includes:
providing a reference signal corresponding to the energy introduced into the pulp slurry; and, comparing the reference signal with each of the signals to provide an output directly proportional to the difference between the reference signal and each of said signals.

30. The method of claim 29 which includes:
ratioing the reference signal to each of the signals received.

31. The method of claim 28 wherein the pulp consistency being measured is between about 2 to 6 percent.

* * * * *

UNITED STATES PATENT OFFICE
CERTIFICATE OF CORRECTION

PATENT NO. : 4,040,743

DATED : August 9, 1977

INVENTOR(S) : Villaume et al.

It is certified that error appears in the above-identified patent and that said Letters Patent are hereby corrected as shown below:

Column 2, line 66;

"$V_B$" should be -- $v_B$ --.

Column 3, line 12;

"independent" should be -- dependent --

Column 5, line 54;

"linerality" should be -- linearlity --.

Column 6, line 33;

"from" should be -- form --.

UNITED STATES PATENT OFFICE
CERTIFICATE OF CORRECTION

PATENT NO. : 4,040,743

DATED : August 9, 1977

INVENTOR(S) : Villaume et al.

It is certified that error appears in the above-identified patent and that said Letters Patent are hereby corrected as shown below:

Column 7, line 55;

"$V_R 1.4$" should be -- $v_R 1.4$ --.

Column 9, claim 1, line 20;

"and" should be -- said --.

Column 12, claim 26, line 29;

"same" should be -- sample --.

Signed and Sealed this

Fifteenth Day of May 1979

[SEAL]

Attest:

RUTH C. MASON
Attesting Officer

DONALD W. BANNER
Commissioner of Patents and Trademarks